US010274711B2

(12) United States Patent
Chiang et al.

(10) Patent No.: US 10,274,711 B2
(45) Date of Patent: Apr. 30, 2019

(54) MICROSCOPIC IMAGE RECOGNITION SYSTEM AND METHOD FOR DETECTING PROTEIN-BASED MOLECULE

(71) Applicant: I Shou University, Kaohsiung (TW)

(72) Inventors: Ching-Fen Chiang, Kaohsiung (TW); Ming-Hung Tsai, Kaohsiung (TW)

(73) Assignee: I SHOU UNIVERSITY, Kaohsiung (TW)

( * ) Notice: Subject to any disclaimer, the term of this patent is extended or adjusted under 35 U.S.C. 154(b) by 0 days.

(21) Appl. No.: 15/654,692

(22) Filed: Jul. 19, 2017

(65) Prior Publication Data

US 2018/0059396 A1    Mar. 1, 2018

(30) Foreign Application Priority Data

Aug. 31, 2016 (TW) .............................. 105128007 A (51) Int. Cl.
*G02B 21/00* (2006.01)
*G01N 33/50* (2006.01)
(Continued)

(52) U.S. Cl.
CPC ......... *G02B 21/0024* (2013.01); *G01N 33/50* (2013.01); *G01Q 30/04* (2013.01);
(Continued)

(58) Field of Classification Search
CPC ........... G01N 15/1475; G01N 33/5035; G01N 33/50; G06K 9/00127; G06K 9/4647;
(Continued)

(56) References Cited

U.S. PATENT DOCUMENTS

| 5,733,721 A | 3/1998 | Hemstreet, III et al. |
| 5,741,648 A | 4/1998 | Hemstreet, III et al. |

(Continued)

FOREIGN PATENT DOCUMENTS

| TW | 201413232 | 4/2014 |
| TW | 1470203 | 1/2015 |

OTHER PUBLICATIONS

Office Action issued by Taiwan Intellectual Property Office dated Apr. 26, 2017.

*Primary Examiner* — Kenny A Cese
(74) *Attorney, Agent, or Firm* — Cheng-Ju Chiang (57) ABSTRACT

A microscopic image recognition system for detecting a protein-based molecule by presenting a recognition image is provided. The protein-based molecule has a state of a monomer. The microscopic image recognition system includes an image capturing unit, a monomer tracking module and a texture mask. The image capturing unit is configured to capture an original image of the protein-based molecule. The monomer tracking module is configured to capture a monomer image from the original image based on a predetermined size and a predetermined brightness. The predetermined size and the predetermined brightness correspond to the monomer. The texture mask is configured to perform a two-dimensional masking process on the monomer image to form at least two texture images. The recognition image is formed by superimposing the at least two texture images. A microscopic image recognition method is also provided.

4 Claims, 6 Drawing Sheets

(51) Int. Cl.
    *G06T 7/00*    (2017.01)
    *G02B 21/36*   (2006.01)
    *G06K 9/62*    (2006.01)
    *G06T 7/44*    (2017.01)
    *G01Q 30/04*   (2010.01)
    *G01Q 30/00*   (2010.01)

(52) U.S. Cl.
    CPC ....... *G02B 21/0036* (2013.01); *G02B 21/367* (2013.01); *G06K 9/62* (2013.01); *G06T 7/0012* (2013.01); *G06T 7/44* (2017.01); *G01Q 30/00* (2013.01); *G02B 21/00* (2013.01); *G06T 2207/30024* (2013.01)

(58) Field of Classification Search
    CPC ........... G06K 9/62; G06T 7/0012; G06T 7/44; G02B 21/0024; G02B 21/0036; G02B 21/367; G01Q 30/04
    See application file for complete search history.

(56) References Cited

U.S. PATENT DOCUMENTS

| | | | |
|---|---|---|---|
| 9,176,043 B2* | 11/2015 | Takagi | G01N 15/1475 |
| 2003/0059093 A1 | 3/2003 | Rosania et al. | |
| 2007/0002067 A1* | 1/2007 | Lefebvre | G06T 3/40 345/582 |
| 2008/0040044 A1 | 2/2008 | Dunlay et al. | |
| 2009/0074275 A1* | 3/2009 | O Ruanaidh | G06K 9/0014 382/128 |
| 2011/0254943 A1 | 10/2011 | Ozinsky et al. | |

\* cited by examiner

FIG. 6

MICROSCOPIC IMAGE RECOGNITION SYSTEM AND METHOD FOR DETECTING PROTEIN-BASED MOLECULE

FIELD OF THE INVENTION

The present invention relates to a microscopic image recognition system and method, and more particularly to a microscopic image detection system and method for detecting protein-based molecules.

BACKGROUND OF THE INVENTION

In the fields of medical and biotechnological science, it is necessary to inspect cells by microscopic images for testing and research. Cell motility or migration is a very important dynamic behavior in cell physiology that may occur in normal tissue growth, repair or disease. Through cell motility or migration, cell physiological situation can be observed.

Cell motility or migration is a dynamic expression of cytoskeleton tension and interaction between cells and extracellular matrix, and actin filaments distributed on the cell membrane are the main supporting tension and the main cytoskeleton components for controlling cell movement.

Microscopic observation of cytoskeleton in the past was performed by using fluorescent immuno-staining technique and confocal microscopy. For example, as disclosed in U.S. Pat. Nos. 9,176,043, 5,741,648 and 5,733,721, the staining must be performed prior to observation of cell or actin filaments. The drawback of such approach is that observation of the distribution and pattern of the actin filaments during cell movement is not possible for that the cells must be fixed for staining. In addition, even after fluorescent staining, structure of the filaments is not clear enough.

Taiwanese Patent No. 1470203 discloses "Image Analysis System and Method for Cancer Cell Recognition," in which spectral analysis is utilized to locate cancer cells. However, even though chemical staining is avoided, the equipment required for spectral analysis is expensive. Therefore, it is necessary to provide a more generalized recognition mean for general cell microscopic imaging, so as to ensure better human physiological health research or treatment. Accordingly, one primary objective of the present invention is to provide a microscopic image recognition system and method for detecting a protein-based molecule to solve the above problems.

SUMMARY OF THE INVENTION

One objective of the present invention is to provide a microscopic image recognition system and a microscopic image recognition method for detecting the protein-based molecule based on the computer vision image technology. Thus, an efficient and general microscopic image recognition mean for cells is obtained.

The present invention provides a microscopic image recognition system for detecting a protein-based molecule by presenting a recognition image. The protein-based molecule has a state of a monomer. The microscope image recognition system includes an image capturing unit, a monomer tracking module and a texture mask. The image capturing unit is configured to capture an original image of the protein-based molecule. The monomer tracking module is configured to capture a monomer image from the original image based on a predetermined size and a predetermined brightness. The predetermined size and the predetermined brightness correspond to the monomer. The texture mask is configured to perform a two-dimensional masking process on the monomer image to form at least two texture images. The recognition image is formed by superimposing the at least two texture images.

In one embodiment, the texture mask includes a weighted average filter and a high-pass filter. The weighted average filter corresponds to a mean vector. The high-pass filter corresponds to an edge-detecting vector. The two-dimensional masking process convolves the edge-detecting vector with a transposition of the mean vector to generate a first mask, convolves the mean vector with a transposition of the edge-detecting vector to generate a second mask, and convolves the monomer image by the first mask and the second mask respectively to obtain the at least two texture images.

In one embodiment, when the texture mask performs the two-dimensional masking process on the monomer image to form four texture images, the first mask is rotated for 45 degrees to the left to generate a third mask, the first mask is rotated for 45 degrees to the right to generate a fourth mask, and the monomer image is convolved by the third mask and the fourth mask to obtain two other texture images of the four texture images.

In one embodiment, the protein-based molecule is an actin filament, and the monomer is a cell.

In one embodiment, for a clustering of the cell, the monomer tracking module is further configured to capture the monomer image from the original image based on a relative change and a morphological analysis.

In one embodiment, the microscopic image recognition system displays the recognition image by a human-machine interface, the recognition image comprises a target image corresponding to the monomer, and the target image is marked with a specific color by selecting the target image via the human-machine interface.

The present invention further provides a microscopic image recognition method for detecting a protein-based molecule by presenting a recognition image. The protein-based molecule has a state of a monomer. The microscopic image recognition method includes steps of: capturing an original image of the protein-based molecule; capturing a monomer image from the original image based on a predetermined size and a predetermined brightness, wherein the predetermined size and the predetermined brightness correspond to the monomer; performing a two-dimensional masking process on the monomer image to form at least two texture images; and superimposing the at least two texture images to form the recognition image.

In one embodiment, the two-dimensional mask processing includes steps of: convolving an edge-detecting vector with a transposition of a mean vector to generate a first mask; convolving the mean vector with a transposition of the edge-detecting vector to generate a second mask; and convolving the monomer image by the first mask and the second mask respectively to obtain the at least two texture images.

In one embodiment, when the at least two texture images are four texture images, the microscopic image recognition method further includes steps of: rotating the first mask for 45 degrees to the left to generate a third mask; rotating the first mask for 45 degrees to the right to generate a fourth mask; and convolving the monomer image by the third mask and the fourth mask respectively to obtain two other texture images of the four texture images.

In one embodiment, for a clustering of the monomer, the step of capturing the monomer image from the original image based on the predetermined size and the predetermined brightness further includes a step of: capturing the monomer image from the original image based on a relative change and a morphological analysis.

In summary, the present invention provides the microscopic image recognition system and the microscope image recognition method for detecting the protein-based molecule based on computer vision technology. The present invention utilizes the monomer tracking module to capture the monomer image of a monomer, such as a cell, the texture mask to perform the two-dimensional masking process on the monomer image to form a plurality of texture images, followed by superimposing the texture images into a clear and dynamically displayed recognition image. Thus, the present invention can efficiently and easily analyze microscopic images of cells.

BRIEF DESCRIPTION OF THE DRAWINGS

Other advantages, objectives and features of the present invention will become apparent from the following description referring to the attached drawings.

DETAILED DESCRIPTION OF PREFERRED EMBODIMENTS

The present invention will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 1:
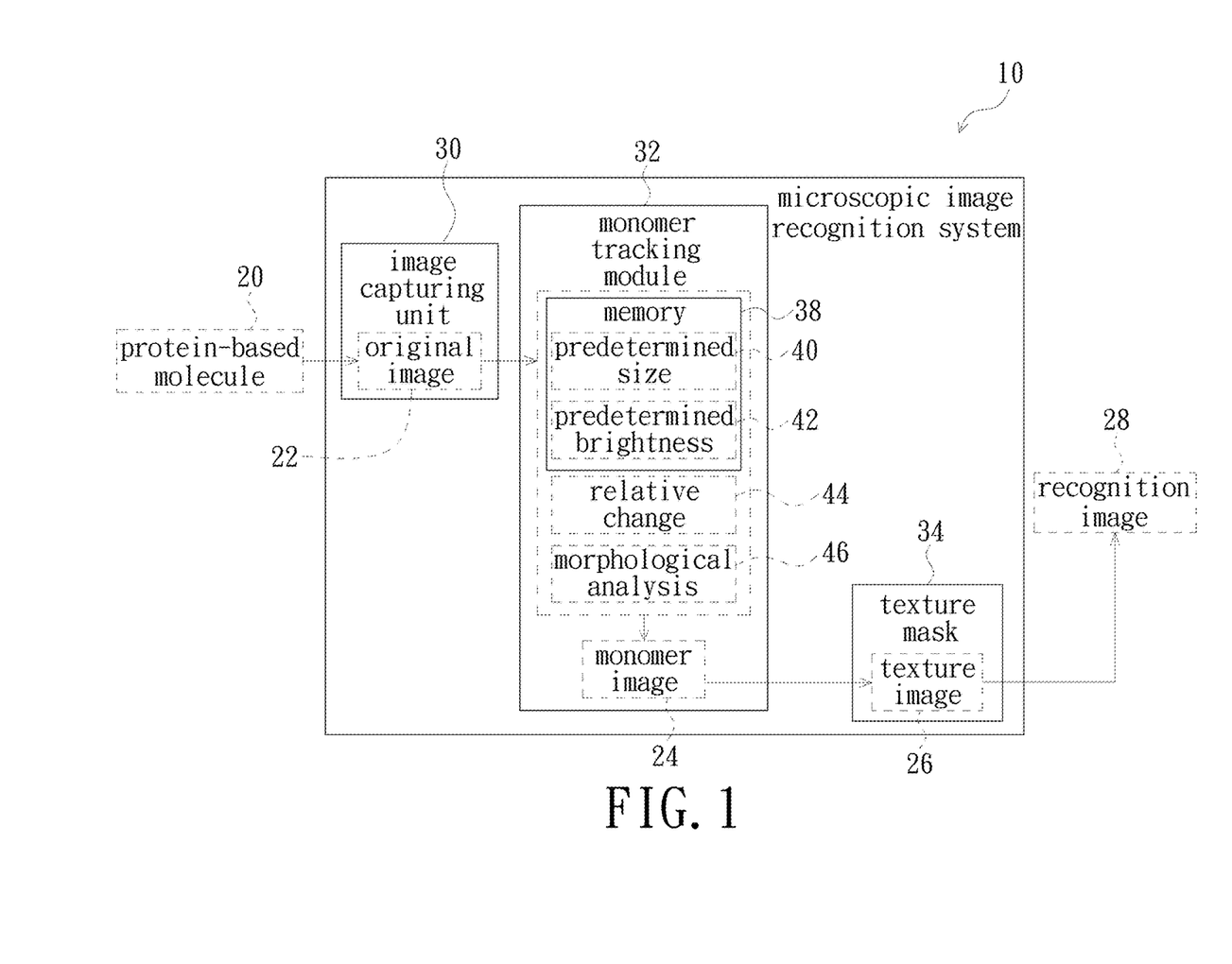
FIG. 1 is a schematic view of a microscopic image recognition system 10 in accordance with an embodiment of the present invention.

Please refer to FIG. 1, which is a schematic view of a microscopic image recognition system 10 in accordance with an embodiment of the present invention. The microscopic image recognition system 10 of the present invention detects a protein-based molecule 20 by presenting a recognition image 28. The protein-based molecule 20 has a monomer state; wherein the protein-based molecule 20 may be an actin filament, and the monomer may be a cell or a tissue. In other words, the microscopic image recognition system 10 of the present invention may detect the actin filaments by analyzing the images of cells.

The microscopic image recognition system 10 includes an image capturing unit 30, a monomer tracking module 32 and a texture mask 34. The image capturing unit 30 may be, for example, an image sensor such as a charge coupled device (CCD) or a complementary metal-oxide-semiconductor transistor (CMOS) for capturing the original image 22 of the protein-based molecule 20 through a microscopic lens (not shown).

The monomer tracking module 32 captures the images of cells from the original image 22 and filters the other image noise to form a monomer image 24 based on a predetermined size 40, a predetermined brightness 42, a relative change 44 and a morphological analysis 46. The predetermined size 40 and the predetermined brightness 42 correspond to the monomer. Specifically, the predetermined size 40 is the size range that the cell image in the original image 22 captured by the image capturing unit 30 should have, and the predetermined brightness 42 is the brightness or grayscale range that the cell image in the original image 22 captured by the image capturing unit 30 should have. The predetermined size 40 and the predetermined brightness 42 are pre-stored in a memory 38 as a basis for comparison. Therefore, the monomer tracking module 32 can filter out the noise image that does not match the predetermined size 40 and the predetermined brightness 42 so as to make the monomer image 24 clearer.

The above is the image recognition approach for an individual cell. However, cells cluster and divide; therefore, for the image recognition of the cells having clustering and division, the monomer tracking module 32 must further capture the images of cells that may have clustering or division from the original image 22 and filter out the other image noise to form the monomer image 24 based on the relative change 44 and the morphological analysis 46. Taking the relative change 44 as an example. There are three cell images in the previous original image 22 having areas A1, A2 and A3 respectively, and only two cell-like images are left in the next original image 22 having areas A1 and A4 respectively. The area A4 is closer to the area (A2+A3), and the distance between the area A4 and the area (A2+A3) is the shortest. Thus, the second cell (having the cell area A2) and the third cell (having the cell area A3) are determined to be clustered into a larger cell. Taking the type analysis 46 as an example. There are two cells in the previous original image 22, and there is one newly-clustered cell in the next original image 22. Because the newly-clustered cell has not yet become a sphere, the perimeter of the newly-clustered cell has an irregular shape and therefore is greater than the perimeter of a sphere with the same area. Thus, by calculating the perimeter of the cell, the two cells in the previous original image 22 can be determined to be clustered into one cell in the next original image 22.

After the determination of cells is completed, the cell tracking module 32 filters out the image noises other than a cell in the original image 22 to form the monomer image 24. Thereafter, the texture mask 34 performs a two-dimensional masking process on the monomer image 24 to form at least two texture images 26. In one preferred embodiment, the number/quantity of the at least two texture images 26 is four and will be described in FIG. 2. Finally, all the at least two texture images 26 are superimposed (i.e., the four texture images 26 are superimposed in the preferred embodiment), and therefore, the recognition image 28 with clear and recognizable cells is obtained.

Figure 2:
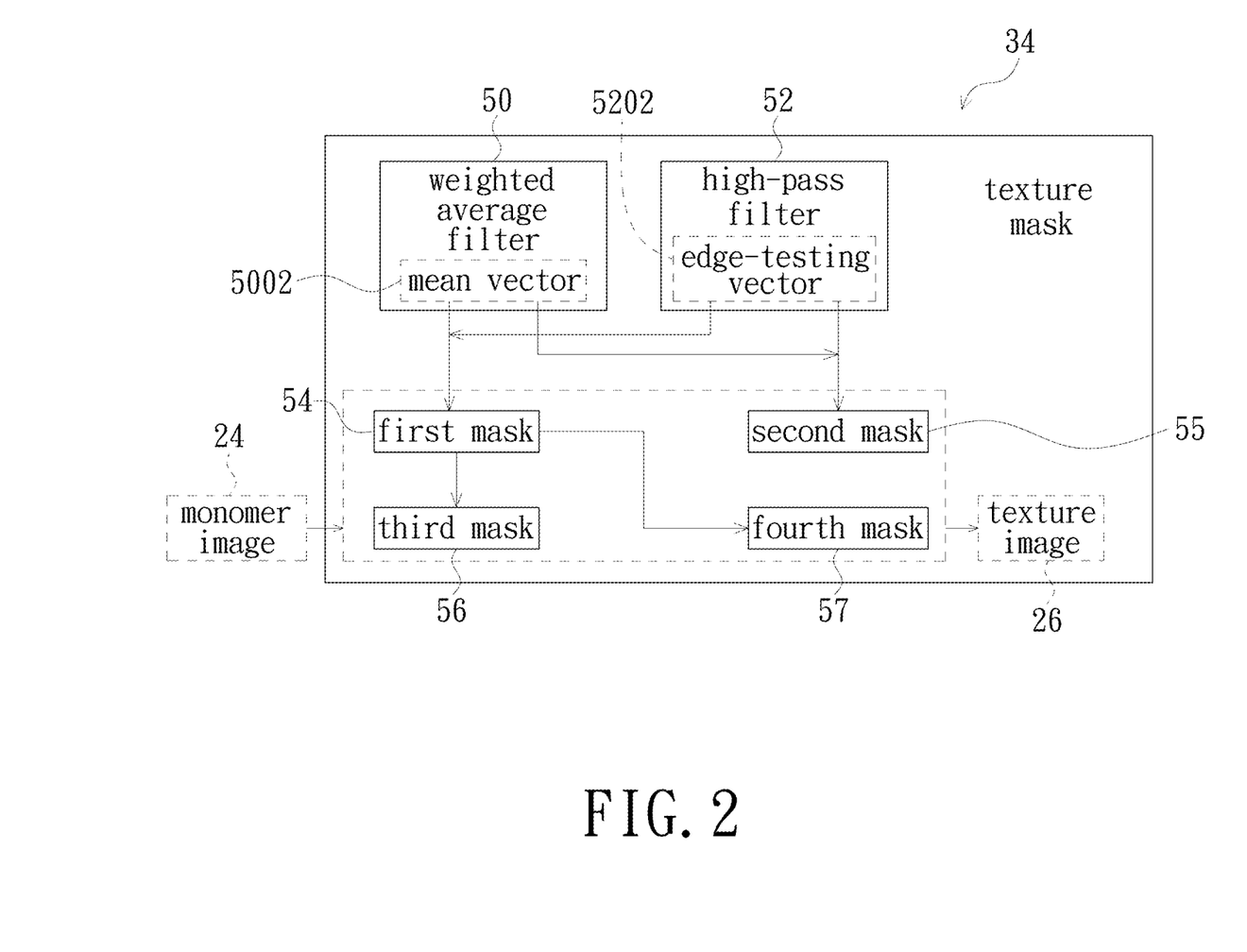
FIG. 2 is a schematic illustration of the texture mask generating the texture images in accordance with an embodiment of the present invention.

Please refer to FIG. 2, which is a schematic illustration of the texture mask 34 generating the texture images 26 in accordance with an embodiment of the present invention. The texture mask 34 includes a weighted average filter 50 and a high-pass filter 52. The weighted average filter 50 corresponds to a mean vector 5002. The mean vector 5002 is for example, (1, 4, 6, 4, 1), which is a one-dimensional vector with odd number of elements (e.g., five elements in the present embodiment). Each sample of pixel signal must contain two signal points respectively located on the right and left of the signal, represent the highest importance with the maximum weight, and then continue to descend on both sides. The high-pass filter 52 corresponds to an edge-detecting vector 5202. The edge-detecting vector 5202 is for example (−1, −2, 0, 2, 1), which is also a one-dimensional vector with five elements. Similarly, each sample of pixel signal located the difference in intensity between the two signal points respectively located on the right and left sides of the midpoint (0), wherein the weight neighboring the midpoint is the highest.

The aforementioned two-dimensional masking process sequentially convolves (i.e., a convolution calculation) the edge-detecting vector 5202 with the transposition of the mean vector 5002 to generate a first mask 54

$$e.g., \begin{pmatrix} \begin{vmatrix} -1 & -2 & 0 & 2 & 1 \\ -4 & -8 & 0 & 8 & 4 \\ -6 & -12 & 0 & 12 & 6 \\ -4 & -8 & 0 & 8 & 4 \\ -1 & -2 & 0 & 2 & 1 \end{vmatrix} \end{pmatrix}$$

that has longitudinal textures, convolves the mean vector with the transposition of the edge-detecting vector 5202 5002 to generate a second mask 55

$$e.g., \begin{pmatrix} \begin{vmatrix} -1 & -4 & -6 & -4 & -1 \\ -2 & -8 & -12 & -8 & -2 \\ 0 & 0 & 0 & 0 & 0 \\ 2 & 8 & 12 & 8 & 2 \\ 1 & 4 & 6 & 4 & 1 \end{vmatrix} \end{pmatrix}$$

that has latitudinal textures, rotates the first mask 54 for 45 degrees to the left to generate a third mask 56

$$e.g., \begin{pmatrix} \begin{vmatrix} 0 & 2 & 1 & 4 & 6 \\ -2 & 0 & 8 & 12 & 4 \\ -1 & -8 & 0 & 8 & 1 \\ -4 & -12 & -8 & 0 & 2 \\ -6 & -4 & -1 & -2 & 0 \end{vmatrix} \end{pmatrix}$$

that has upper-left-to-lower-right textures, rotates the first mask 54 for 45 degrees to the right to generate a fourth mask 57

$$e.g., \begin{pmatrix} \begin{vmatrix} -6 & -4 & -1 & -2 & 0 \\ -4 & -12 & -8 & 0 & 2 \\ -1 & -8 & 0 & 8 & 1 \\ -2 & 0 & 8 & 12 & 4 \\ 0 & 2 & 1 & 4 & 6 \end{vmatrix} \end{pmatrix}$$

that has upper-right-to-lower-left textures, and then respectively convolves the grayscale of the monomer image 24 by the first mask 54, the second mask 55, the third mask 56 and the fourth mask 57 to obtain the four texture images 26.

The process of forming the recognition image 28 by superimposing the four texture images 26 will be described as follow. The value obtained by convolving the grayscale of the monomer image 24 by each one of the first mask 54, the second mask 55, the third mask 56 and the fourth mask 57 may exceed the numerical range of the general display grayscale 0-255. The aforementioned superimposition refers to adding and averaging the grayscales of the four convolved texture images 26; however, the averaged numerical range may still exceed the numerical range of the general display grayscale 0-255. Therefore, in addition to the step of adding and averaging the grayscales of the four convolved texture images 26, all the averaged numerical values must be adjusted by the same ratio to locate the averaged numerical range in the general display grayscale 0-255, thereby normally displaying the recognition image 28 with clear and recognizable cells.

Figure 3:
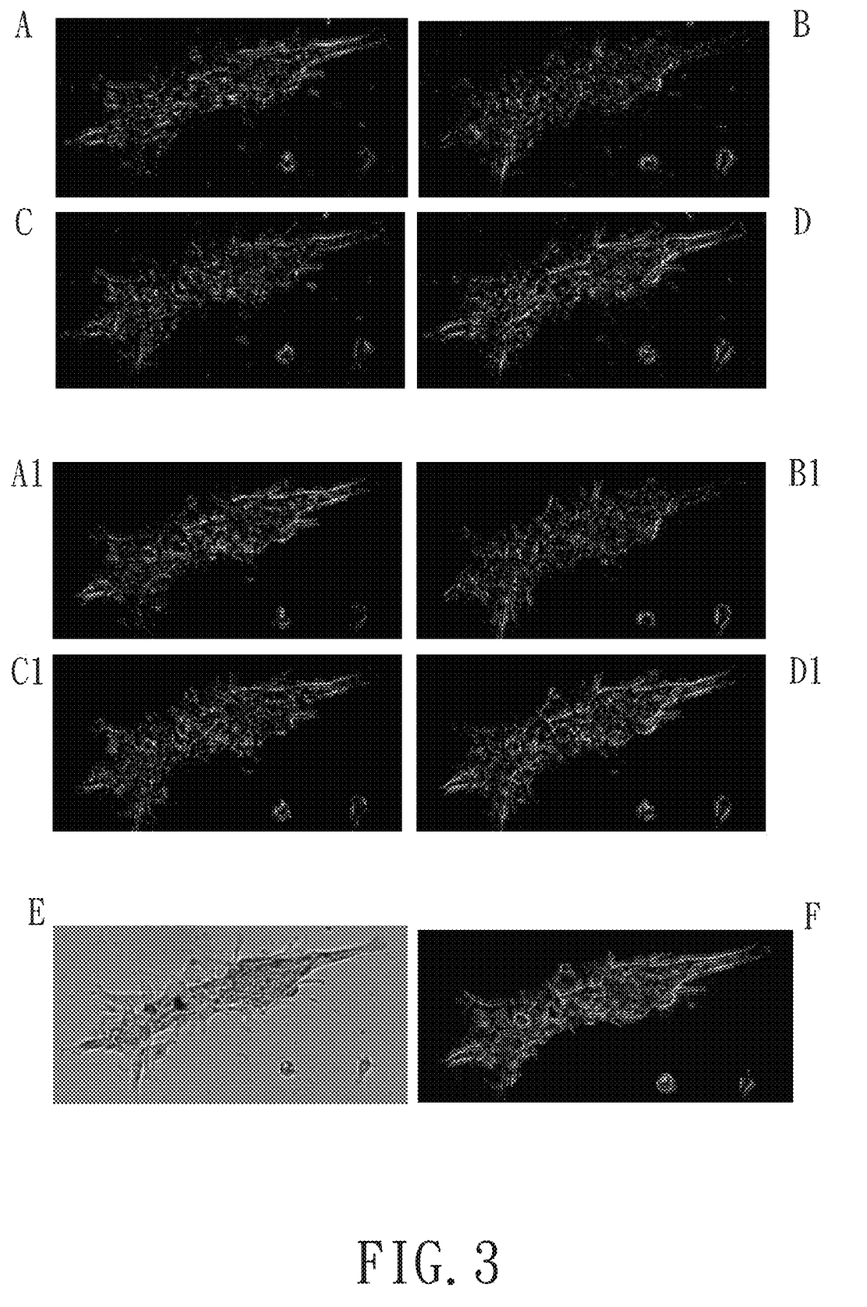
FIG. 3 is four texture images and the recognition image.

Please refer to FIG. 3, which shows the four texture images 26, the original image 22 and the recognition image 28. The sub-views A, B, C and D in the upper part of FIG. 3 are the four texture images 26 not processed by the monomer tracking module 32. In other words, the texture mask 34 directly processes the four texture images 26 of the sub-views A, B, C and D with the original image 22, without processing the monomer image 24. And therefore as shown in the sub-views A, B, C and D, the noise signal is relatively strong, which may lead to difficulties in the following visual analysis or digital quantization analysis. The sub-views A1, B1, C1 and D1 in the middle part of FIG. 3 are the four texture images 26 after processed by the monomer tracking module 32 of the present invention. As shown, there is no noise signal in the sub-views A1, B1, C1 and D1. Therefore, compared with the original image 22 (i.e., the image E shown in FIG. 3), the recognition image 28 (i.e., the image F shown in FIG. 3) with clear and recognizable cells is obtained by superimposing the four texture images 26 of the sub-views A1, B1, C1 and D1 without any noise signal.

In addition, since the imaging principle of the present invention is completely different from the conventional technique for statically staining cells, a dynamic image for motility or migration of the cells is generated in the present invention by successively displaying a plurality of recognition images 28, so the observation and analysis of cell state is improved. Due to such effect, the microscopic image recognition system 10 may further use a human-machine interface to display the recognition image 28, wherein the recognition image 28 includes a target image corresponding to one aforementioned monomer. The human-machine interface may be a touch display screen, in which touch is used as the input mode of the human-machine interface; or the human-machine interface may be a general screen, in which items are selected and inputted by moving the mouse. By using the human-machine interface to select the target image, the selected target image can be marked with a specific color, so as to facilitate observation of the changes during the process of cell clustering and division from the dynamic image.

Figure 4:
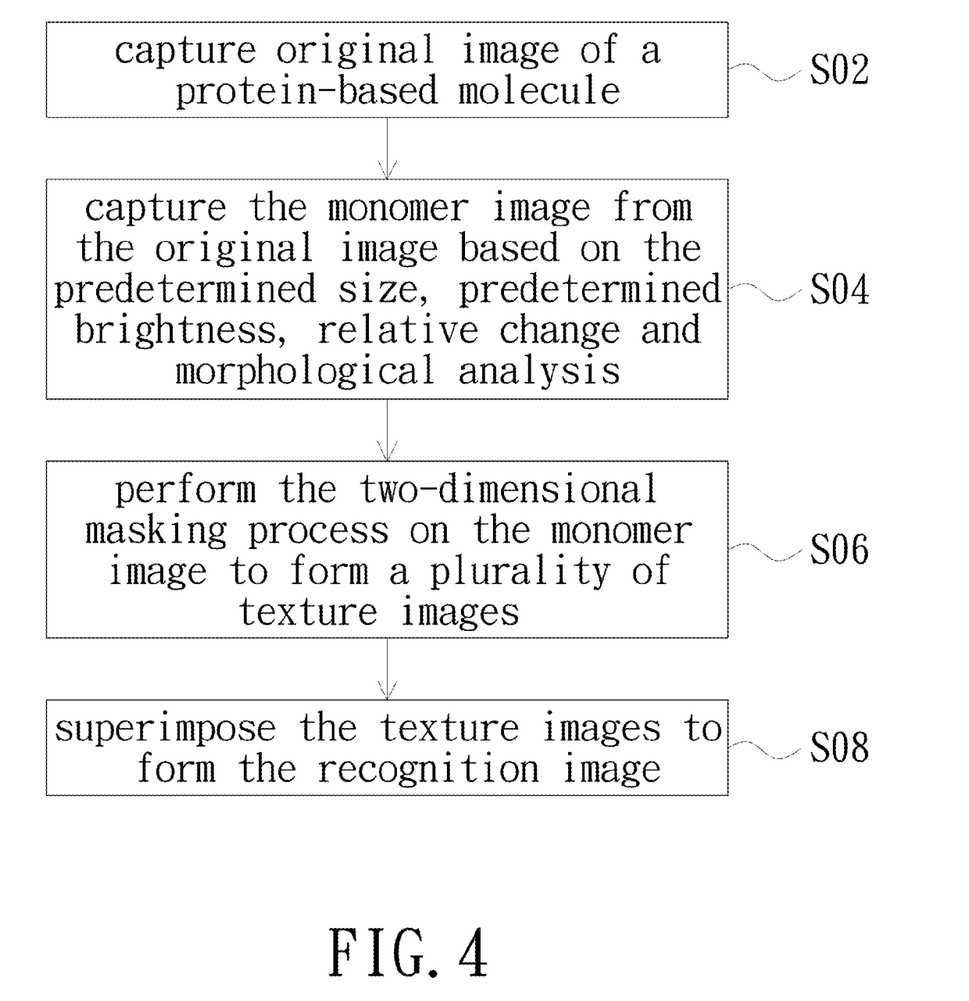
FIG. 4 is a flowchart of a microscopic image recognition method in accordance with an embodiment of the present invention.

Please refer to FIG. 4, which is a flowchart of a microscopic image recognition method in accordance with an embodiment of the present invention. The microscopic image recognition method of the present invention is adapted to the aforementioned microscopic image recognition system 10 for detecting the protein-based molecule 20. Specifically, the microscopic image recognition method detects the protein-based molecule 20 by presenting the recognition image 28. The protein-based molecule 20 has a monomer state. The microscopic image recognition method includes steps of: capturing the original image 22 of the protein-based molecule 20 (step S02); capturing the monomer image 24 from the original image 22 based on the predetermined size 40, the predetermined brightness 42, the relative change 44 and the morphological analysis 46, wherein the predetermined size 40 and the predetermined brightness 42 correspond to the monomer (step S04); performing the two-dimensional masking process on the monomer image 24 to form at least two texture images 26 (step S06); and superimposing the at least two texture images 26 to form the recognition image 28 (step S08).

Figure 5:
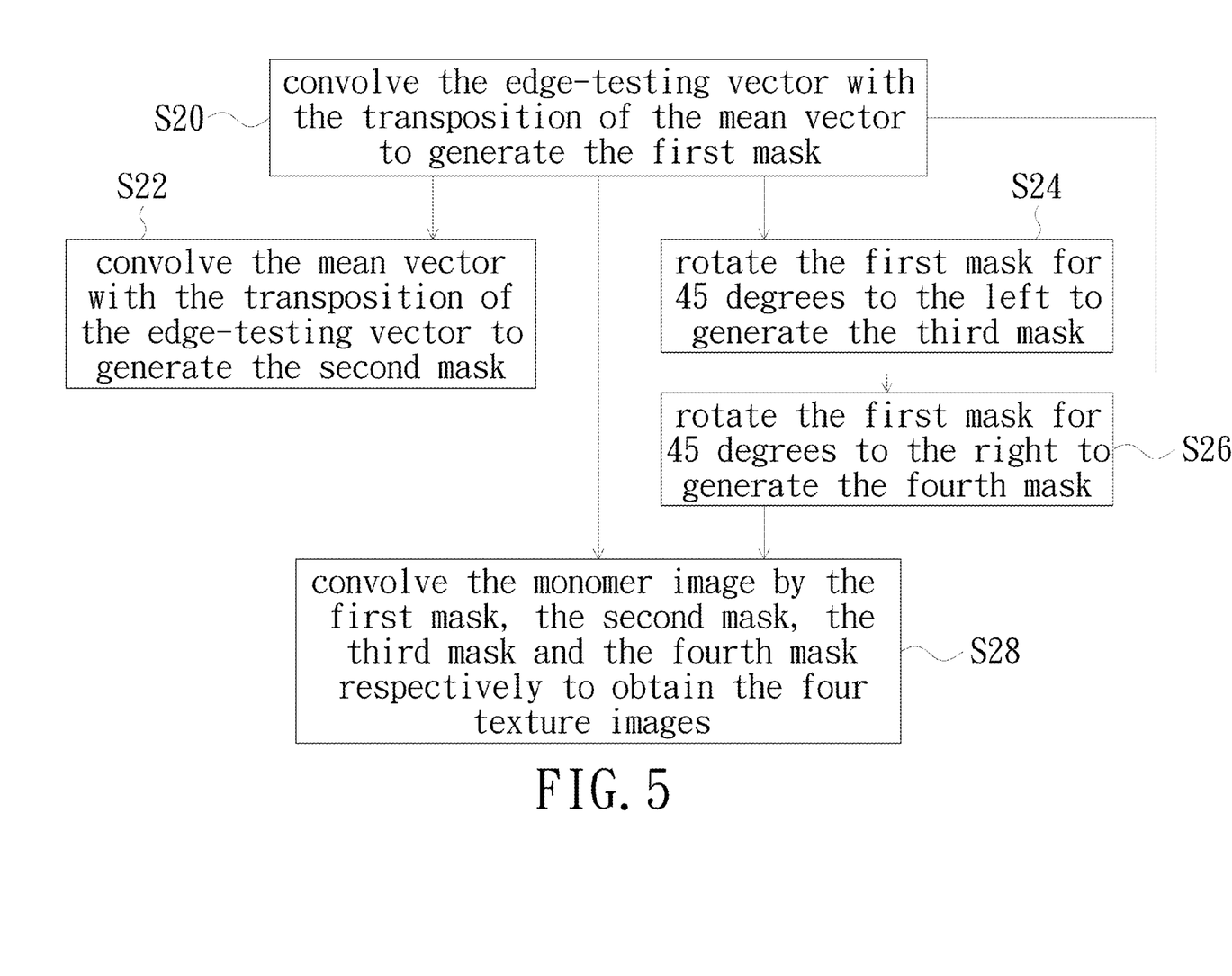
FIG. 5 is a flow chart of a method of the two-dimensional masking process in accordance with an embodiment of the present invention.

Please refer to FIG. 5, which is a flow chart of a method of the two-dimensional masking process in accordance with an embodiment of the present invention. In the following preferred embodiment, the method of the two-dimensional masking process is exemplified by four texture images 26. The two-dimensional masking process includes steps of: convolving the edge-detecting vector 5202 with the transposition of the mean vector 5002 to generate the first mask 54 (step S20); convolving the mean vector 5002 with the transposition of the edge-detecting vector 5202 to generate the second mask 55 (step S22); rotating the first mask 54 for 45 degrees to the left to generate the third mask 56 (step S24); rotating the first mask 54 for 45 degrees to the right to generate the fourth mask 57 (step S26); and convolving the monomer image 24 by the first mask 54, the second mask 55, the third mask 56 and the fourth mask 57 respectively to obtained the four texture images 26 (step S28).

Figure 6:
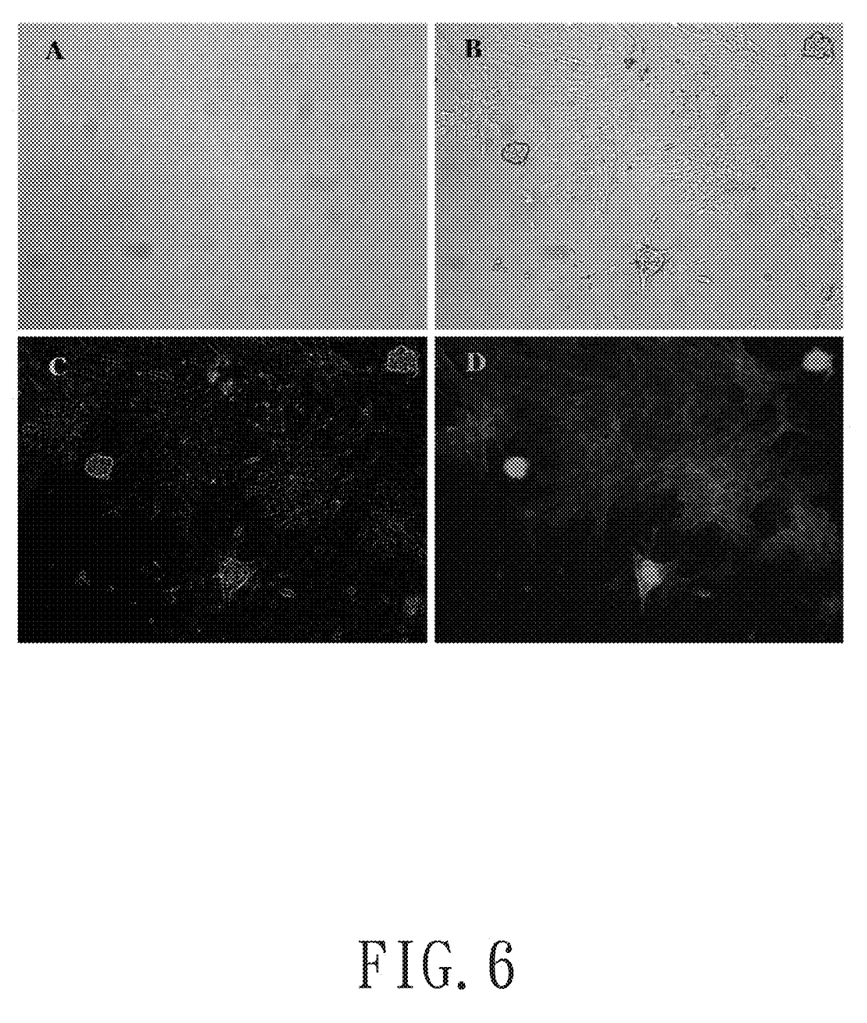
FIG. 6 schematically shows four images for system validation.

Please refer to FIG. 6, which shows the four images. Specifically, the sub-view A: the background image without cell but with some speckle noises; the sub-view B: cell image; the sub-view C: the texture image extracted by our method; and the sub-view D: the actin filament obtained by using fluorescent immune-staining. The texture pattern in the sub-view C is identical to the actin filament in the sub-view D. In addition, the noises shown in the sub-view A have been removed in the sub-view C. This figure shows the validity of the proposed method to reveal the actin filament in cells using general light microscopy without the need of staining.

In summary, the present invention provides the microscopic image recognition system 10 and the microscopic image recognition method for detecting the protein-based molecule 20 based on computer vision image technology. In the present invention, the monomer tracking module 24 captures the monomer image 24 of a monomer, such as a cell, and the texture mask 34 performs the two-dimensional masking process on the monomer image 24 to form a plurality of texture images 26 and superimposes the texture images 26 into the clear and dynamically displayed recognition image 28. Thus, the present invention can efficiently and easily analyze microscopic images of cells.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A microscopic image recognition method for detecting a protein-based molecule by presenting a recognition image, the protein-based molecule having a state of a monomer, and the microscopic image recognition method comprising steps of:
    capturing an original image of the protein-based molecule;
    capturing a monomer image from the original image based on a predetermined size and a predetermined brightness, wherein the predetermined size and the predetermined brightness correspond to the monomer;
    performing a two-dimensional masking process on the monomer image to form at least two texture images; and
    superimposing the at least two texture images to form the recognition image.

2. The microscopic image recognition method according to claim 1, wherein the two-dimensional mask processing comprises steps of:
    convolving an edge-detecting vector with a transposition of a mean vector to generate a first mask;
    convolving the mean vector with a transposition of the edge-detecting vector to generate a second mask; and
    convolving the monomer image by the first mask and the second mask with respectively to obtain the at least two texture images.

3. The microscopic image recognition method according to claim 2, wherein when the at least two texture images are four texture images, the microscopic image recognition method further comprises steps of:
    rotating the first mask for 45 degrees to the left to generate a third mask;
    rotating the first mask for 45 degrees to the right to generate a fourth mask; and
    convolving the monomer image by the third mask and the fourth mask with respectively to obtain two other texture images of the four texture images.

4. The microscopic image recognition method according to claim 1, wherein for a clustering of the monomer, the step of capturing the monomer image from the original image based on the predetermined size and the predetermined brightness further comprises a step of:
    capturing the monomer image from the original image based on a relative change and a morphological analysis.

* * * * *